(12) United States Patent
de Jong et al.

(10) Patent No.: US 7,491,410 B2
(45) Date of Patent: Feb. 17, 2009

(54) FOOD GRADE TRANSGLUTAMINASE INHIBITOR AND USES THEREOF

(75) Inventors: Govardus Adrianus Hubertus de Jong, Hoogland (NL); Johannes Wilhelmus Leonardus Boumans, Ouderkerk aan de Amstel (NL); Gerrit Wijngaards, Drempt (NL)

(73) Assignee: Nederlandse Organisatie Voor Toegepast-Natuurwetenschappelijk Onderzoek TNO, Delft (NL)

( * ) Notice: Subject to any disclaimer, the term of this patent is extended or adjusted under 35 U.S.C. 154(b) by 263 days.

(21) Appl. No.: 10/415,584

(22) PCT Filed: Oct. 30, 2001

(86) PCT No.: PCT/NL01/00795

§ 371 (c)(1),
(2), (4) Date: Aug. 11, 2004

(87) PCT Pub. No.: WO02/35942

PCT Pub. Date: May 10, 2002

(65) Prior Publication Data

US 2005/0031603 A1    Feb. 10, 2005

(30) Foreign Application Priority Data

Oct. 31, 2000   (EP)   .................. 00203778

(51) Int. Cl.
  *A61K 38/43*   (2006.01)
  *A61K 35/20*   (2006.01)

(52) U.S. Cl. ................. 424/535; 424/94.1; 424/400

(58) Field of Classification Search ............... 424/94.1, 424/400, 535; 435/183
See application file for complete search history.

(56) References Cited

U.S. PATENT DOCUMENTS 5,098,707 A    3/1992   Baldwin et al. ........... 424/94.64
5,198,213 A    3/1993   Stott et al. ................. 424/85.8
5,695,753 A *  12/1997  Stief et al. ............... 424/94.63

FOREIGN PATENT DOCUMENTS

| EP | 0 610 649 | 8/1994 |
|---|---|---|
| WO | WO 93/19610 | 10/1993 |
| WO | WO 95/17426 | 6/1995 |
| WO | WO 98/09717 | 3/1998 |
| WO | WO 98/48640 | 11/1998 |
| WO | WO 99/45027 | 9/1999 |
| WO | WO 99/65515 | * 12/1999 |
| WO | WO 99/65516 | 12/1999 |
| WO | WO 00/40231 | * 7/2000 |

OTHER PUBLICATIONS

Kogen, H., Kiho, T., Tago, K., Miyamoto, S., Fujioka, T., Otsuka, N., Suzuki-konagai, K., Ogita, T., 2000. J. Am. Chem. Soc., 122:1842-1843.
Zhu, Y., Rinzema, A., Tramper, J., Bruin, E.de. and Bol, J. (1998) Appl. Micr. Biotech. 49, 251-257.
Zhu, Y., Rinzema, A., Tramper, J., J Appl. Microbial Biotechnol (1995) 44: 277-282.
Tymiak, A.A., Tuttle, J.G., Kimball, S.D., Wang, T. Lee, V.G. (1993) J. Antibiot. 46:204-206.
Ando, H., Adachi, M., Umeda, K., Matsuura, A., Nonaka, M., Uchio, R., Tanaka, H. and Motoki, M. (1989) Agric. Biol. Chem. 53, 2613-2617.
Lorand, L., Lockridge, O.M., Campbell, L.K., Myhrman, R. and Bruner-Lorand, J. (1972) Anal. Biochem. 44, 221-231.
Laemmli, U.K. (1970) Nature 227, 680-685.
Folk, J.E. and Cole, P.W. (1965) J. Biol. Chem. 241, 2951.

* cited by examiner

*Primary Examiner*—Ruth A Davis

(57) ABSTRACT

Transglutaminase inhibitor containing composition obtainable from milk, in particular from a whey fraction obtainable from skimmed milk by forming a curd from the milk, separating the curd from the whey in a centrifugation step followed by subjecting the whey to an ultrafiltration step or, alternatively, by subjecting the skimmed milk to a diafiltration step, a method for the production of a transglutaminase inhibitor and the use of the transglutaminase inhibitor in the production of food or pharmaceutical compositions and to the use in the preparation of a medicament for the treatment of pathologies.

13 Claims, 4 Drawing Sheets

A

B

FOOD GRADE TRANSGLUTAMINASE INHIBITOR AND USES THEREOF

The present invention is directed to a transglutaminase inhibitor that is obtainable from milk, a method for obtaining said transglutaminase inhibitor from milk, the use of said transglutaminase inhibitor in regulating the cross-linking of proteins and its use in food products or in pharmaceutical compositions and to the use of said transglutaminase inhibitor in the preparation of a medicament for the treatment of certain diseases.

Transglutaminase (protein-glutamine-γ-glutamyltransferase, EC 2.3.2.13) catalyses acyl transfer reactions introducing covalent cross-linkages between proteins, thereby creating high molecular weight molecules. Transglutaminases are a group enzymes, some of which being $Ca^{2+}$ dependent, that catalyse the formation of isopeptide bonds between the side chains of glutamine and lysine residues. When a lysine bound to a protein serves as the primary amine donor, the reaction results in the formation of an ε-(γ-glutamyl)-lys isopeptide bond that serves to cross-link the proteins. The resulting bond is covalent, stable and is considered relatively resistant to proteolysis. The enzymes have been isolated and purified from a variety of sources, among which bacteria, fungi, plants and mammals (Zhu, Y., Rinzema, A., Tramper, J., J. Appl. Microbial Biotechnol (1995) 44: 277-282). The biological role and structural features of the transglutaminases derived from different sources differ enormously, but they all contain a cystein in the active site responsible for the cross-linking reaction and therefore the cross-linking of proteins is one feature that all types of transglutaminase have in common. Among the transglutaminases, plasma glutaminase (Factor XIIIa) from mammals and humans is one of the best studied enzymes. This enzyme plays a crucial role in the blood clotting pathway as the enzyme cross-links fibrin molecules to enhance the strength of the fibrin networks in blood-clots. Another type of transglutaminase, also from mammals and humans, is generally depicted as tissue transglutaminase. This type of transglutaminase has been shown to be involved in a number of processes like Huntington's disease, apoptosis, celiac disease and Alzheimer's disease. Other processes in which transglutaminases play a role are dermatological afflictions, cataract, spinobulbar atrophy (Kennedy's disease), (spino)cerebellar ataxia, dentatorubral-pallidoluysian atrophy, inflammatory diseases of the central nervous system, including multiple sclerosis, rheumatoid arthritis, diabetes such as insulin dependent diabetes mellitus, tetanus and other *Clostridium* related pathologies, Rett's syndrom, HIV infections and inflammatory processes.

The discovery of a $Ca^{2+}$-independent bacterial transglutaminase from a *Streptovertillium* strain has given the research on transglutaminase a big boost, because of the possibility of producing the enzyme in large amounts. As the enzyme has become available in large amounts there is currently an increasing interest in the application of the enzyme in various fields of technology.

Some of the applications of transglutaminase are in the preparation of food and protein ingredients for food. The protein cross-linking activity of the enzyme can be used to improve the texture and structure of food products and the functional properties of proteins. EP-A-0 610 649 discloses the use of transglutaminase in the production of yoghurt. WO 93/19610 describes the use of transglutaminase in milk, thereby providing a product with improved consistency.

Because of the large number of biological processes in which transglutaminases are involved and the increased use of transglutaminase, there is a widespread interest in compounds that modify or inhibit the activity of transglutaminases. Several inhibitors, among which monodansyl cadaverine, mono-and diamines such as cystamine, putrescine, GABA (gamma-amino benzoic acid), N-benzyloxy carbonyl, 5-deazo-4-oxonorvaline, p-nitrophenylester, glycine methyl ester, $CuSO_4$ and tolbutamide have been described in WO 99/65516 for use in the treatment of various pathologies. Amines such as spermine and spermidine have been referred to as substrates for transglutaminase. Inhibitors such as monodansyl cadaverine, putrescine, spermine, spermidine and glycine methylester are primary amines that inhibit the protein cross-linking activity of transglutaminase through competition reactions, they do not block the transglutaminase activity. Other well-known transglutaminase inhibitors, such as N-ethylmaleimide, iodoacetate and parachloromercuribenzoic acid, are known to work by covalently blocking the active site cystein of transglutaminase. However, these compounds are known to be toxic and hence not suitable for application in food and food ingredients. Other transglutaminase inhibitors described in the patent literature are isoxazoles, imidazoles (U.S. Pat. No. 5,098,707), and thiadiazoles (WO-A-99/45027).

Natural inhibitors of transglutaminase are scarce. Certain specific peptides are known to inhibit transglutaminase (WO-A 95/17426). An antimicrobial agent produced by a fungus, cerulinin, is reported as a natural non-peptide inhibitor of plasma transglutaminase (Tymiak, A. A., Tuttle, J. G., Kimball, S. D., Wang, T. Lee, V. G. (1993) J. Antiobiot. 46:204-206). Alutacenoic acids, isolated from fungi have also shown activity as potent inhibitors of plasma transglutaminase (Kogen, H., Kiho, T., Tago., K., Miyamoto, S., Fujioka, T., Otsuka, N., Suzuki-konagai, K., Ogita, T., 2000. J. Am. Chem. Soc. 122:18421-18430.)

One of the disadvantages of the use of transglutaminases in foods is that the products in which the enzyme remains present in an active form may have a negative health effect. It is therefore preferred that the activity of the enzyme is controlled prior to the consumption of the product. Preferably the control of the enzyme occurs to the extent that the enzyme is completely inhibited or inactivated.

The inactivation of the enzyme can be achieved by thermal treatment of the product. However, thermal treatment of products in many cases may lead to unwanted changes in the characteristics of the products. In the case of foods, this may lead to a product that is less attractive for the consumer. The transglutaminase inhibitors that are presently known in the art are in general compounds or compositions that, mostly due to their toxicity, are not allowed, or otherwise regarded as unsuitable for application in foods. Accordingly, a need exists for a transglutaminase inhibitor that is suitable for application in foods (i.e. food-grade) and at the same time provides for an effective inhibition of the activity of the transglutaminase while adverse effects of the inhibitor on either the product or the consumer are at least substantially reduced or absent.

The present inventors have now found that milk contains an inhibitor of transglutaminase. They found in cross-linking experiments of skimmed milk with transglutaminase only a very small degree of formation of higher molecular weight casein polymers. Intensive heat treatment of the skimmed milk resulted in a much higher degree of cross-linking as was observed by the formation of large polymers and the disappearance of casein monomers. Removal of casein and whey proteins from the milk resulted in a fraction in which the transglutaminase inhibiting activity was retained. They also found that this inhibitor not only inhibits bacterial transglutaminase but is also effective in inhibiting the activity of two transglutaminases that are present in blood. By a combination of isolation and purification steps, the inhibitor can be partly purified while the inhibiting activity remains and the fraction thus obtained can be used in the inhibition of transglutaminase.

The invention, in a first aspect, provides for a transglutaminase inhibitor containing composition obtainable from milk, in particular from a whey fraction obtainable from milk, preferably from skimmed milk. In a first embodiment, the inhibitor is obtainable from whey obtained by (i) subjecting milk to an acid treatment and subsequent removing the precipitated proteins by the acid treatment leaving a whey fraction, or (ii) by forming a curd from the milk, for instance by use of micro-organisms or proteases, separating the curd from the whey in a centrifugation step, followed by subjecting the whey obtained to an ultrafiltration step. In an alternative embodiment, the inhibitor is obtainable by subjecting milk to a diafiltration step.

By subjecting the whey fraction obtainable from milk to an ultrafiltration step, the desired fraction containing the transglutaminase inhibitor is obtained in the permeate which is separated from the whey proteins. Preferably, the whey fraction is ultrafiltrated using a membrane with a cut-off of 10 kDa. The limit of the cut-off of the membrane is determined by the capability to remove two of the major whey proteins α-lactalbumin (14.1 kDa) and β-lactoglobulin (18 kDa). As the inhibitor according to the present invention is thought to have a molecular weight in the order of about 200 Da, a suitable cut-off will be from 1 kDa, but cut-offs of 2, 3 4 or 5-10 kDa are also suitable.

In case the desired fraction containing the transglutaminase inhibitor is obtained by diafiltration, it is preferred that the diafiltration membrane has a cut-off of about 3 kDa. However, a suitable membrane for diafiltration will have a cut-off in the same range as the membrane for ultrafiltration, ranging from 1-10 kDa.

The invention, in a second aspect, provides for a method for obtaining a transglutaminase inhibitor containing composition from milk, in particular from a whey fraction, comprising the steps of forming a curd from the milk, separating the curd from the whey in a centrifugation step followed by subjecting the whey to an ultrafiltration step. Preferably the curd is formed by acidifying the milk with a food-grade acid such as hydrochlorid acid, malic acid, tartaric acid, citric acid, lactic acid or glucone (delta glucone), or as an alternative by addition of acid generating microorganisms. Alternatively, the process encompasses subjecting the skimmed milk to a diafiltration step.

In U.S. Pat. No. 5,198,213, it is described that the top fraction of whey, which top fraction contains the higher molecular weight proteins contains a measurable but low level of immunologically active immunoglobulin plus other pathogen specific antibodies. No reference is made to any useful applications of the low molecular weight compounds containing whey fractions associated with transglutaminase.

WO-A-98/48640 discloses an insulin-free protein fraction, which consists of larger proteins. These fractions are used in infant formulae and other nutritive preparations.

In WO-A-98/09717 a particular separation technique is described. In examples 3 and 4 proteins are recovered from milk and whey, respectively. No particular uses in accordance with the present invention of the said products are given, especially not for the low molecular weight fractions.

The transglutaminase inhibitor containing composition, which will also be referred to as transglutaminase inhibitor, according to the invention is thought to be a low molecular weight material, preferably with a molecular weight in the order of magnitude of about 200 Dalton.

With respect to the characteristics of the transglutaminase inhibitor according to the invention, it has been found that the inhibitor is not a free metal ion.

The inhibitor according to the invention inhibits the activity of transglutaminase in the cross-linking of casein and other proteins and in several activity assays of transglutaminase. The inhibitor may be used in the form of the whey fraction. It is preferred to subject the fraction containing the inhibitor to a concentration step. A suitable concentration step is lyophilisation or spray drying. In this embodiment of the invention, the inhibitor is obtained in a concentrated form while the inhibiting capability of the inhibitor is not substantially affected. Re-dissolving the dried product from the lyophilisation step and/or the spray drying step results in the inhibiting effect on transglutaminase being largely maintained.

In a further embodiment of the invention the inhibitor may be further purified. Suitable purification steps are gel filtration and/or ion exchange techniques. When purifying the inhibitor, preferably at least part of the lactose is removed.

The inhibitor according to the invention is stable over a wide temperature range. The isolation and purification and concentration steps by which the inhibitor is obtained can be carried out at temperatures up to about 80° C. Care should be taken not to exceed the upper limit of this temperature range. Exceeding the upper temperature limit, in general, results in loss or undesirable reduction of the activity of the transglutaminase inhibitor. Preferably the inhibitor is not heated to temperatures of above 70° C., more preferably of above 60° C.

The inhibitor according to the present invention may be isolated from milk. Milk from which a fraction containing the inhibitor according to the invention can be obtained comes from animals and preferably domestic animals such as cow, goat, sheep, horse, camel, buffalo, deer, ass, reindeer; it is in principle also possible to use human milk as a suitable source. In a preferred embodiment the inhibitor is obtained from cow's milk. Preferably the milk is untreated or at least not extensively heat treated. The fatty fraction is preferably removed, e.g. by centrifugation. Proteins are preferably removed through ultrafiltration, precipitation and/or diafiltration or a combination of these techniques; the inhibitor composition is in the permeate of the ultrafiltration and diafiltration step.

The inhibitor according to the invention binds in a substantially covalent fashion to the transglutaminase as has been shown by MALDI-TOF analysis. Furthermore it has been found by titration experiments that the inhibitor binds in a approximately equimolar amount to transglutaminase. Without wishing to be bound to any particular theory, it is thought that the inhibitor according to the invention is bound to transglutaminase cystein residues.

The invention finds application in the production of food and food products. When transglutaminase is used in the cross-linking of proteins to improve the structure of protein containing foods, for instance foods such as dairy (yoghurt), meat or fish, the transglutaminase activity can be stopped or reduced by the addition of the inhibitor according to the invention. In one aspect, the invention relates to the use of the transglutaminase inhibitor in the production of food.

An important aspect of the inhibitor according to the invention is the use of the inhibitor in the regulation of the degree of cross-linking. It has been found that partial cross-linking of β-casein results in the formation of a gel when heated, whereas uncross-linked β-casein or extensively cross-linked β-casein does not form a gel on heating. Regulation of the degree of cross-linking is easily achieved by the addition of the inhibitor according to the invention whereas other means for activation, for instance through heating, may very well destroy protein functionality. Furthermore the inhibitor according to the invention may be used in a form that allows for controlled release, such as encapsulation. It can easily be envisaged that the addition of transglutaminase in combination with (micro)encapsulated inhibitor to a substrate will result in the homogenous distribution of both transglutaminase and inhibitor. Cross-linking of the proteins can then be governed by the release profile of the inhibitor. This is advantageous when the product after cross-linking is viscous or gelated.

The invention pertains in a further aspect to a pharmaceutical composition comprising the transglutaminase inhibitor according to the invention. The pharmaceutical composition can be advantageously used in the treatment of diseases that are in any way associated with or related to transglutaminase activity. The pharmaceutical composition according to the invention can comprise at least one transglutaminase inhibitor in a pharmaceutically acceptable form, optionally combined with a pharmaceutical acceptable carrier. These compositions can be administered by any means that achieve their intended purposes. Amounts and regimens for the administration of a transglutaminase inhibitor according to the invention for the treatment of diseases mediated by transglutaminase activity can readily be determined by those with ordinary skill in the art of treating these diseases.

The invention further relates to the use of the transglutaminase inhibitor in the preparation of a medicament for the treatment of diseases in which transglutaminase plays a role such as for example Alzheimer's disease, haemophilia, apoptosis, celiac disease, Huntington's disease, dermatological afflictions, cataract, spinobulbar atrophy (Kennedy's disease), (spino)cerebellar ataxia, dentatorubral-pallidoluysian atrophy, inflammatory diseases of the central nervous system, including multiple sclerosis, rheumatoid arthritis, diabetes such as insulin dependent diabetes mellitus, tetanus and other *Clostridium* related pathologies, Rett's syndrom, HIV infections and inflammatory processes.

EXAMPLES

Materials and Methods

Figure 1:
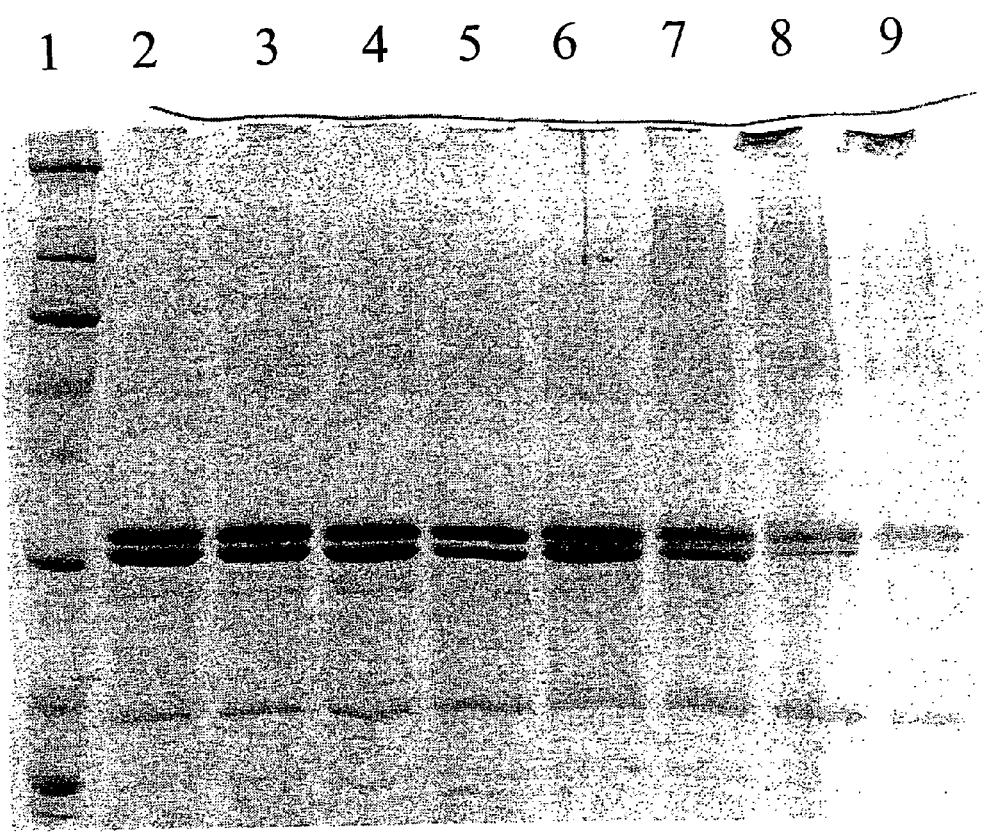
FIG. 1: Cross-linking of skimmed milk with bacterial transglutaminase (30 µg/ml, before and after heat treatment (3 h, 80° C.).
  Lane 1 Molecular weight markers
  Lane 2 untreated skimmed milk+transglutaminase, t=0 min;
  Lane 3 untreated skimmed milk+transglutaminase, t=10 min;
  Lane 4 untreated skimmed milk+transglutaminase, t=30 min;
  Lane 5 untreated skimmed milk+transglutaminase, t=120 min;
  Lane 6 heated skimmed milk+transglutaminase, t=0 min;
  Lane 7 heated skimmed milk+transglutaminase, t=10 min;
  Lane 8 heated skimmed milk+transglutaminase, t=30 min;
  Lane 9 heated skimmed milk+transglutaminase, t=120 min.

Materials. Source Q, Source S and Superdex peptide 30 were purchased from Pharmacia (Uppsala, Sweden). Biogel P2 was obtained from BioRad. N,N,-Dimethyl casein, casein, Cbz-glutaminylglycine, hydroxylamine and guinea pig liver transglutaminase were obtained from Sigma. All other reagents were of analytical grade. Skimmed milk was obtained from a local shop, fresh milk directly from a farm. *Streptoverticillium mobaraense* was grown as described [1] and purification of transglutaminase was performed according to [2]. Human plasma transglutaminase was obtained from Behring Werke.

Cross-linking of Skimmed Milk Proteins

Skimmed milk proteins were cross-linked by the addition of 30 µg bacterial transglutaminase per ml skimmed milk. As a control, skimmed milk was incubated at 80° C. for 3 hours prior to the addition of transglutaminase. Incubations were performed at 37° C., and samples were taken at time intervals. The cross-linking reaction was terminated by incubation at 80° C. for 5 min. Analyses of the cross-linking reactions were performed by gel electrophoresis.

Measurement of Transglutaminase Inhibition Using Activity Assays

Quantitative analysis of inhibition of bacterial and guinea pig transglutaminase activity was determined with the hydroxamate assay [3]. 30 µl (1 mg/ml) transglutaminase was incubated with variable amounts of inhibitor fraction (0 to 30 µl). The mixture was incubated at room temperature for 30 min, to ensure coupling of the inhibitor to the transglutaminase. Activity measurements were performed with the inhibited fractions.

Quantitative analysis of inhibition of plasma transglutaminase activity was determined by the incorporation of monodansylcadaverine into dimethylated casein according to Lorand [4]. Plasma transglutaminase was measured in this assay, because this enzyme does not show any activity in the hydroxamate assay. Dithiotreitol was omitted from the reaction mixture in order to prevent possible removal of the inhibitor from the transglutaminase through reduction. Inhibition was calculated from the relative decrease in activity.

Measurement of Transglutaminase Inhibition Using Cross-linking Experiments

Qualitative analyses of inhibition of bacterial transglutaminase activity was determined with cross-linking of casein. 20 µg transglutaminase was incubated with 200 µl of the ultrafiltrated inhibitor fraction. The mixture was incubated at room temperature for 30 min, to ensure coupling of the inhibitor to the transglutaminase. The standard reaction mixture (total volume of 2 ml) contained 50 mM sodium acetate pH 6, 10 mg/ml casein, and 10 µg pre-incubated transglutaminase. Incubations were performed at 40° C., and samples were taken at time intervals. The reaction was terminated by incubation at 80° C. for 5 min. Analyses of the cross-linking reactions were performed by gel electrophoresis.

Polyacrylamide-gel electrophoresis (SDS-PAGE). Subunit molecular masses were determined under denaturing conditions by SDS-PAGE according to Laemmli (5) using ready gels and Mini Protean equipment (Bio-Rad). Enzyme or reaction mixture samples were denatured by incubation for 5 min. at 100 C in 2% SDS and 1% dithiotreitol. Gels were stained for protein with Coomassie Brilliant Blue G250. A high molecular weight calibration kit (Pharmacia) was used to derive the molecular masses.

Preparation of a Substantially Protein-free Inhibitor Fraction

Procedure 1

Skimmed milk was brought to pH 4.4 by addition of hydrochloric acid. Precipitated casein was removed by centrifugation (20 min 25000 g). The clear supernatant was ultrafiltrated using a 10 kDa membrane (Amicon). The concentrated whey proteins were removed and the solution that has passed the membrane was frozen or lyophilised The inhibitor could be further purified by gel filtration on a Superdex 30 peptide column or Biogel P2 to remove lactose and other non inhibitory components.

Procedure 2

1 litre of skimmed milk was dialysed against 5 liter of demineralized water using a dialysis tube with a cut off of 3500 Da. After 24 hours dialysis, the dialysis tube containing the protein fraction was removed. The solution containing the molecules of lesser size than 3500 contained the transglutaminase inhibitor. This fraction can be lyophilised in order to concentrate the inhibitor. Solutions of the inhibitor can be prepared by dissolving the lyophilised sample in water. Residual non dissolving compounds were removed by centrifugation.

Maldi TOF Analysis of Transglutaminase Before and After Inhibition

Bacterial transglutaminase (1 mg) was incubated with 10 ml of inhibition fraction obtained by procedure 1. After 30 min of incubation at room temperature the inhibition of transglutaminase was tested in the hydroxamate assay. The inhibited transglutaminase was ultrafiltrated using a 30 kDa Amicon filter to remove unbound components and concentrate the bacterial transglutaminase. Molecular masses of the inhibited transglutaminase and of the blank were measured using Maldi TOF.

Results

Cross-linking of Skimmed Milk Proteins

SDS/PAGE analysis after cross-linking of skimmed milk showed only little indication of cross-linking (FIG. 1). The skimmed milk after heat treatment at 80° C. for 3 hours, however, showed normal cross-linking of the caseins. Extra addition of transglutaminase to the unheated skimmed milk resulted in cross-linking, comparable to the heated skimmed milk (data not shown).

Measurement of Transglutaminase Inhibition Using Activity Assays

Figure 2:
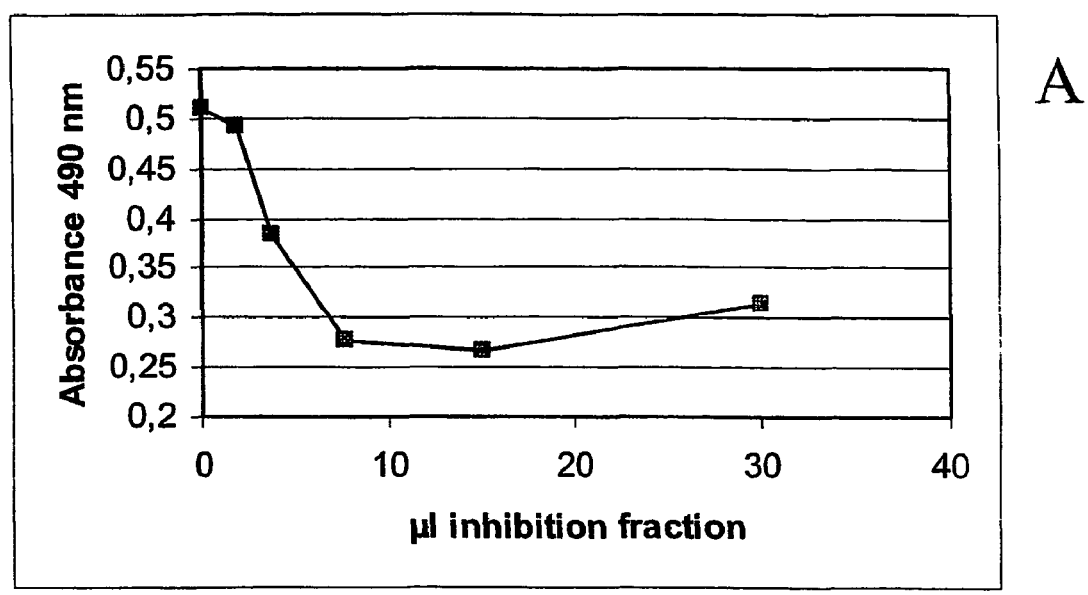
FIG. 2: Activity assay of bacterial transglutaminase after incubation with the inhibitor fraction.
  A: bacterial transglutaminase after incubation with the inhibitor fraction obtained through ultrafiltration of the whey fraction.
  B: bacterial transglutaminase after incubation with the inhibitor fraction obtained through gelfiltration of the whey fraction.
Figure 2:
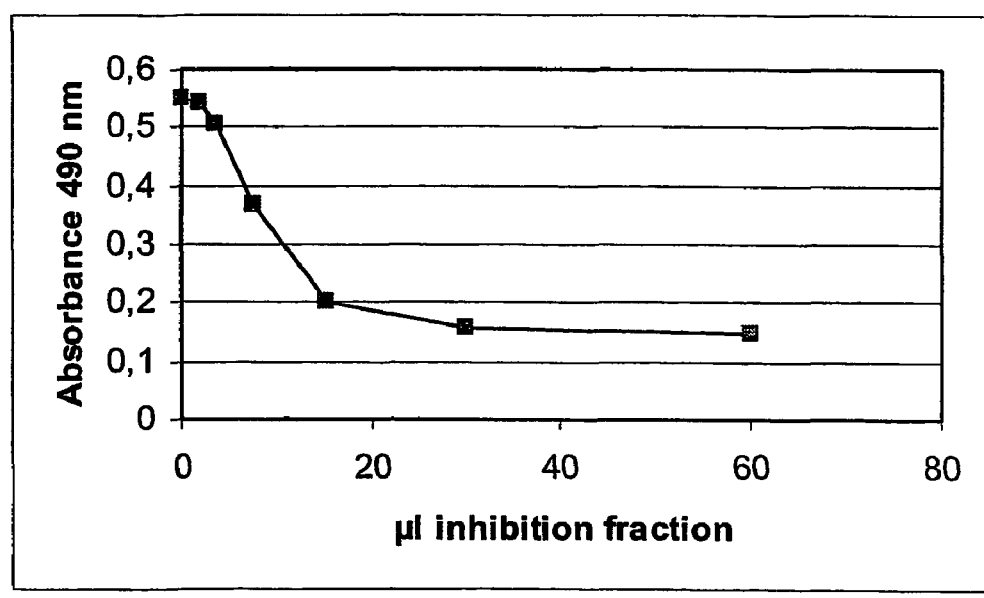

Activities of bacterial transglutaminase after incubation with the inhibitor fraction were lowered as could be observed in the hydroxamate assay (FIG. 2a). Depending on the type of inhibitor fraction used, components present in the fraction were responsible for disturbances in the activity measurements. These components caused colour formation that interfered with the absorbance measurements of the transglutaminase activity. Further purification of the inhibitor on gel filtration removed the interfering compounds which results in an linear inhibition curve (FIG. 2b).

Guinea pig liver transglutaminase gave similar results (data not shown).

Activities of plasma transglutaminase after incubation with the inhibitor fraction were lowered as could be observed in the fluorescence assay (data not shown). This result clearly shows that it is possible to completely inactivate plasma transglutaminase by the inhibitor.

Measurement of Transglutaminase Inhibition Using Cross-linking Experiments

Figure 3:
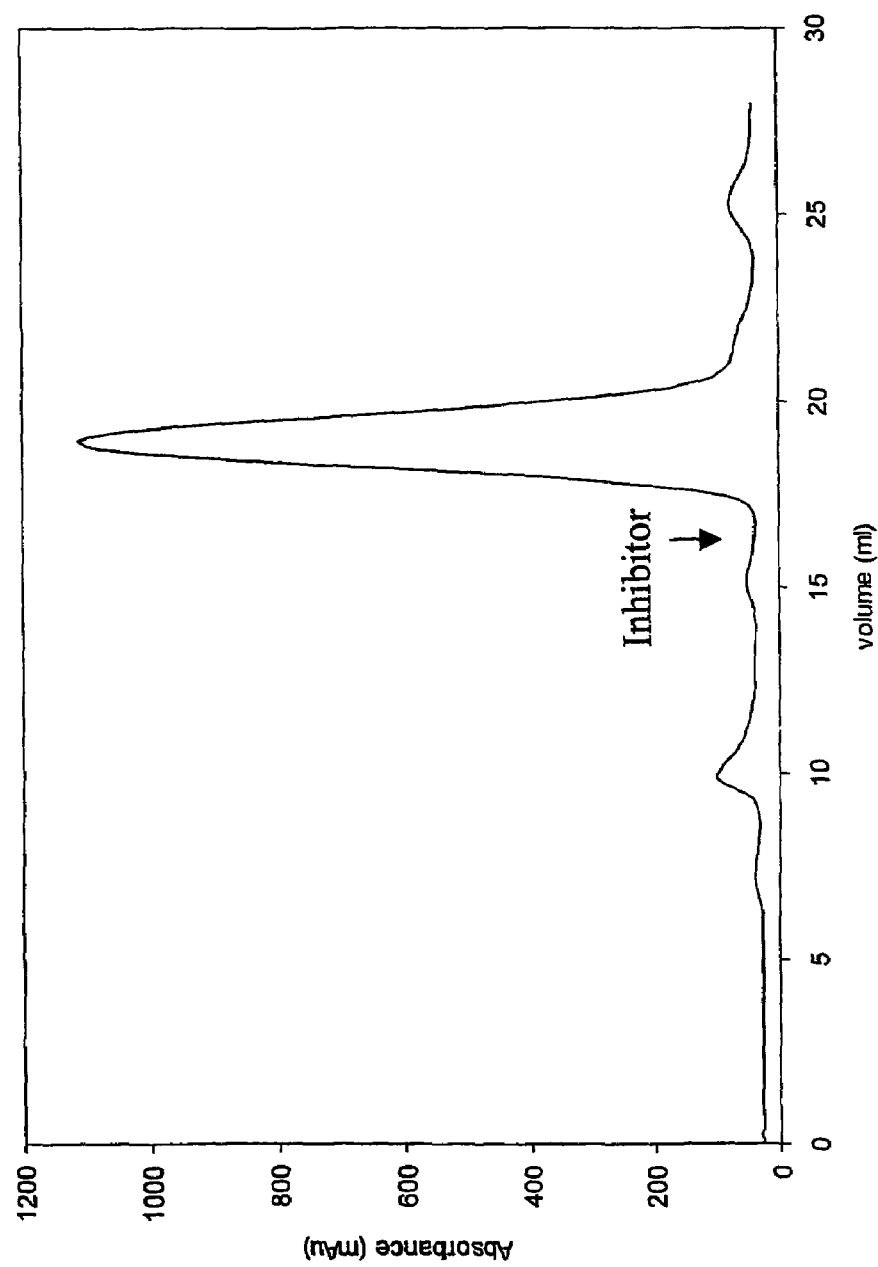
FIG. 3: Separation of protein free inhibitor fraction on Biogel P2. The inhibitor fraction was obtained by procedure 1. The position where the inhibitor eluted is depicted in the figure.

Cross-linking of casein was not observed with bacterial transglutaminase after inhibition with the fraction obtained after procedure 1 (FIG. 3). The control with untreated transglutaminase showed normal cross-linking.

Preparation of a Protein Free Inhibitor Fraction

Procedure 1

Figure 4:
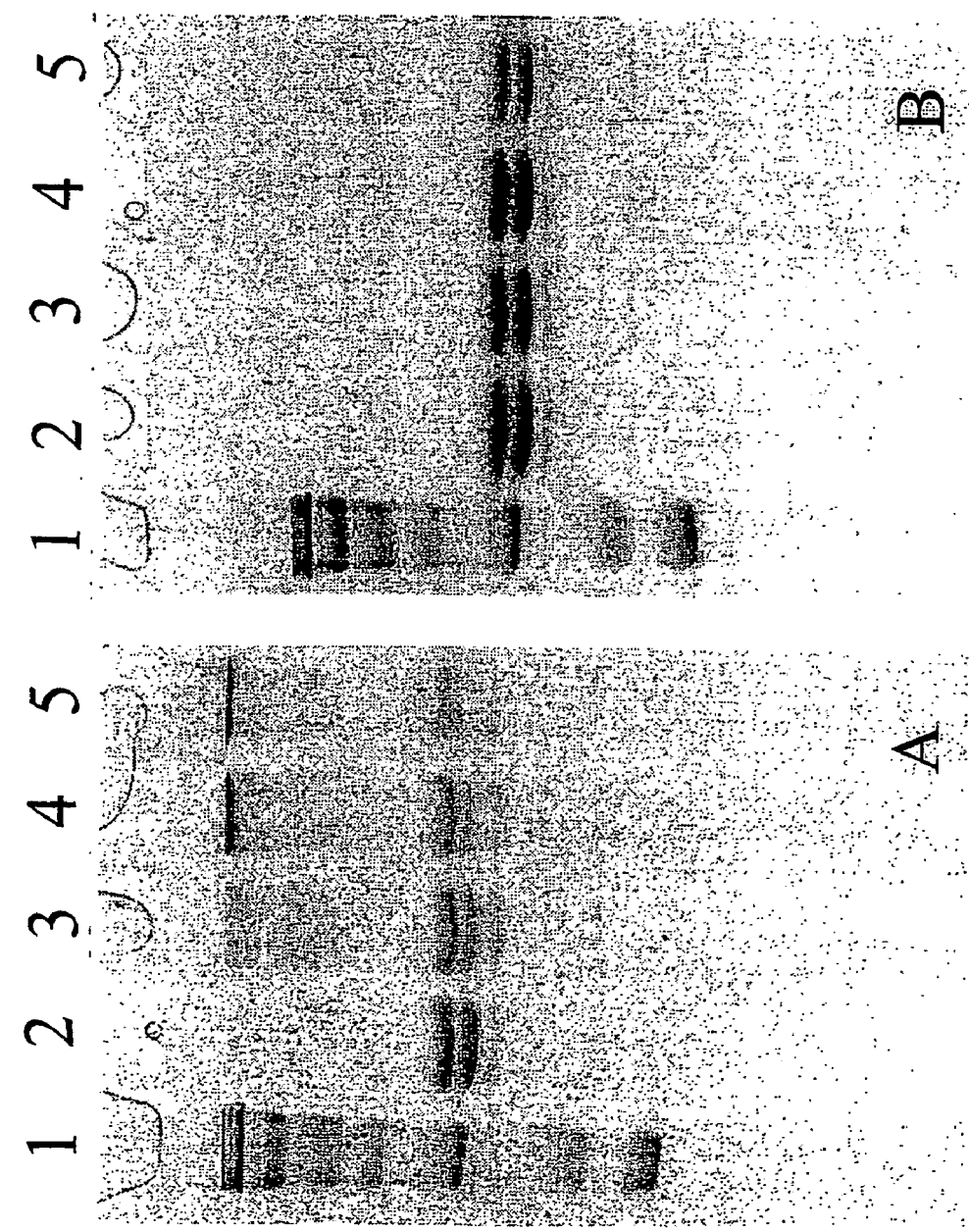
FIG. 4 Cross-linking of casein with untreated bacterial transglutaminase and with bacterial transglutaminase preincubated with a protein free inhibitor fraction.
  A: Cross-linking of casein with untreated transglutaminase
    Lane 1 molecular weight marker
    Lane 2 casein after cross-linking with transglutaminase t=0 min;
    Lane 3 casein after cross-linking with transglutaminase t=10 min;
    Lane 4 casein after cross-linking with transglutaminase t=20 min;
    Lane 5 casein after cross-linking with transglutaminase t=40 min.
  B: Cross-linking of casein with transglutaminase after preincubation with inhibitor.
    Lane 1 molecular weight marker
    Lane 2 casein after cross-linking with transglutaminase t=0 min;
    Lane 3 casein after cross-linking with transglutaminase t=10 min;
    Lane 4 casein after cross-linking with transglutaminase t=20 min;
    Lane 5 casein after cross-linking with transglutaminase t=40 min.

Caseins were removed by centrifugation after precipitation at pH 4.4. The whey protein fraction was subsequently ultrafiltrated using a 10 kDa ultrafiltration unit (Amicon). The low molecular weight fraction that passed the membrane showed transglutaminase inhibition as can be seen in FIG. 2a. Concentration of this fraction was achieved by lyophilisation of the solution and dissolving the solids in a small volume of water. The concentrated fraction was further purified on a Biogel P2 (FIG. 4).

Procedure 2

Caseins and whey protein were separated from the inhibitor fraction through dialysis of the skimmed milk. The proteins remained in the dialysis tube, whereas the inhibitor together with other low molecular weight components passed the dialysis membrane. The dialysis procedure caused dilution of the inhibitor, therefore the solution was lyophilised and the solids dissolved in a small volume of water.

Maldi TOF Analysis of Trans Glutaminase

The molecular weight of transglutaminase as determined with Maldi TOF was 37.900 Da, the molecular weight of the inhibited transglutaminase was 38.064 Da. Because it is possible that only a part of the inhibitor is coupled to the transglutaminase, the mass obtained does not have to correspond to the mass of the inhibitor.

REFERENCES

1 Ando, H., Adachi, M., Umeda, K., Matsuura, A., Nonaka, M., Uchio, R., Tanaka, H. and Motoki, M. (1989) *Agric. .Biol. Chem* 53, 2613-2617
2 Zhu, Y., Rinzema, A., Tramper, J., Bruin, E.de. and Bol, J. (1998) *Appl. Micr.Biotech.* 49, 251-257
3 Folk, J. E. and Cole, P. W (1965). *J. Biol. Chem.* 241, 2951
4 Lorand, L., Lockridge, O. M., Campbell, L. K., Myhrman, R. and Bruner-Lorand, J. (1972) *Anal. Biochem.* 44, 221-231

5 Laemuli, U. K. (1970) *Nature* 227, 680-685

The invention claimed is:

1. Method of preparing a medicament, comprising the steps of (i) obtaining a transglutaminase inhibitor-containing composition from milk, which composition has the property of blocking the activity of transglutaminase and (ii) providing the composition in an acceptable form so as to form a medicament.

2. The method according to claim 1, wherein step (i) comprises
   (A) the steps of: (I) obtaining a whey fraction from skimmed milk by forming a curd from the milk, (II) separating the curd from the whey in a centrifugation step, and (III) subjecting the whey to an ultrafiltration step to form a filtrate; or
   (B) subjecting skimmed milk to a diafiltration step to form a filtrate.

3. The method according to claim 2, further comprising subjecting the filtrate to a concentration step.

4. The method according to claim 3, wherein the concentration step comprises lyophilisation.

5. The method according to claim 2, further comprising at least partially further purifying the whey fraction in a purification step comprising one or both of gel filtration and ion exchange chromatography.

6. The method according to claim 5, wherein the purification step comprises removal of at least part of the lactose present in the whey.

7. The method according to claim 2, wherein curd is formed by the acidification of the milk with food grade acid or by the addition of acid generating micro-organisms.

8. The method according to claim 7, wherein the milk is acidified to a pH of 2.8-5.2.

9. The method according to claim 1, wherein the milk is derived from a domestic animals or a human.

10. The method according to claim 1, whereby the milk has been heat treated at a temperature lower than 80° C.

11. The method according to claim 1, wherein the transglutaminase inhibitor has a molecular weight in the order of magnitude of about 200 Dalton.

12. The method according to claim 1, wherein the medicament is for treatment of Alzheimer's disease, haemophilia, apoptosis, celiac disease, Huntington's disease, dermatological afflictions, cataract, spinobulbar atrophy (Kennedy's disease), (spino) cerebellar ataxaia, dentatorubral-pallidoluysian atrophy, inflammatory diseases of the central nervous system, including multiple sclerosis, rheumatoid arthritis, diabetes such as insulin dependent diabetes mellitus, tetanus and Rett's syndrome, HIV infections and inflammatory processes.

13. The method of claim 1, wherein the composition has the further property of binding to transglutaminase.

* * * * *